(12) United States Patent
Sidoti et al.

(10) Patent No.: US 10,402,541 B2
(45) Date of Patent: Sep. 3, 2019

(54) COLLABORATIVE ELECTRONIC NOSE MANAGEMENT IN PERSONAL DEVICES

(71) Applicant: INTERNATIONAL BUSINESS MACHINES CORPORATION, Armonk, NY (US)

(72) Inventors: Stefano Sidoti, Rome (IT); Alessandro Donatelli, Rome (IT); Fabio Benedetti, Rome (IT); Filomena Ferrara, Rome (IT); Arcangelo Di Balsamo, Rome (IT)

(73) Assignee: International Business Machines Corporation, Armonk, NY (US)

( * ) Notice: Subject to any disclaimer, the term of this patent is extended or adjusted under 35 U.S.C. 154(b) by 279 days.

(21) Appl. No.: 14/912,409

(22) PCT Filed: Aug. 20, 2014

(86) PCT No.: PCT/EP2014/067720
§ 371 (c)(1),
(2) Date: Feb. 17, 2016

(87) PCT Pub. No.: WO2015/028364
PCT Pub. Date: Mar. 5, 2015

(65) Prior Publication Data
US 2016/0210425 A1    Jul. 21, 2016

(30) Foreign Application Priority Data
Aug. 28, 2013   (GB) ................................. 1315251.7

(51) Int. Cl.
*G06F 19/00*    (2018.01)
*G16H 50/20*    (2018.01)
*G01D 1/14*    (2006.01)

(52) U.S. Cl.
CPC ......... *G06F 19/3418* (2013.01); *G16H 50/20* (2018.01); *G01D 1/14* (2013.01); *Y02A 90/26* (2018.01)

(58) Field of Classification Search
CPC ....................................................... G01N 33/03
See application file for complete search history.

(56) References Cited

U.S. PATENT DOCUMENTS 6,422,061 B1 *   7/2002   Sunshine ............. G01N 29/022
                                                      340/603
8,641,611 B2     2/2014   Urushihata et al.
(Continued)

FOREIGN PATENT DOCUMENTS

CN       1737571 A      2/2006
EP       2 273 427 A     12/2011
(Continued)

OTHER PUBLICATIONS

International Search Report & Written Opinion for PCT/EP2014/067720, dated Nov. 5, 2014 (8 pages).

*Primary Examiner* — Matthew D Krcha
(74) *Attorney, Agent, or Firm* — Heslin Rothenberg Farley & Mesiti P.C.; Michael O'Keefe, Esq.

(57) ABSTRACT

A system and diagnosis server are provided for collaborating with electronic noses, as well as a related mobile diagnosis unit and related method. The diagnosis server includes a receiver unit for receiving a set of data from one e-nose of a plurality of e-noses. The set of data may include a sensor identifier, a sensor output value, and a relevance flag for a predefined diagnosis. In addition, a determination unit determines a probability factor for the predefined diagnosis based on the set of data, a relevance function and a distribution function.

6 Claims, 5 Drawing Sheets

(56) References Cited

U.S. PATENT DOCUMENTS

| | | |
|---|---|---|
| 2001/0037070 A1 | 11/2001 | Cranley et al. |
| 2003/0186461 A1* | 10/2003 | Boehr ................ G01N 33/0034 436/181 |
| 2004/0135684 A1* | 7/2004 | Steinthal ................ B82Y 30/00 340/522 |
| 2006/0229820 A1* | 10/2006 | Kemp ................ G01N 33/0034 702/19 |
| 2007/0198222 A1 | 8/2007 | Schuster et al. |
| 2012/0016252 A1 | 1/2012 | Melker et al. |
| 2014/0330103 A1 | 11/2014 | Yoo |

FOREIGN PATENT DOCUMENTS

| | | |
|---|---|---|
| JP | H 08-313408 A | 11/1996 |
| JP | H 10-118046 A | 5/1998 |
| JP | 2006-309465 A | 11/2006 |
| WO | WO2000/52444 A2 | 9/2000 |
| WO | WO2000/79243 A1 | 12/2000 |
| WO | WO 2001/08554 A1 | 2/2001 |

\* cited by examiner

COLLABORATIVE ELECTRONIC NOSE MANAGEMENT IN PERSONAL DEVICES

BACKGROUND

The present invention relates generally to a system including a diagnosis server for collaboration with electronic noses, and to a mobile diagnosis unit for collaboration with the diagnosis server. The invention relates further to a diagnosis method for collaborating using electronic noses.

The field of electronic noses is becoming one of the more interesting technologies from a research and investment point of view. Electronic noses (in short: e-nose) keep airports and, for instance, the space station, safe by noticing the tiniest amounts of dangerous chemicals. They can tell the difference between things like different beverages that taste the same, bad apples and good ones, cancer cells and normal cells, even different qualities of wine may be detectable by electronic noses. All of them use a number of sensors, but even the more sophisticated ones have no more than eight sensors simultaneously active. Besides, due to higher volume and reduced prices, more units will be sold and used.

Price and physical volume are key issues when e-noses are used in smart devices, like smart mobile phones, and the like.

In most cases, software analyzes the patterns of each sensor to determine what the smell is, but the software is only able to elaborate a static set of input values, the one provided by the sensors, and in a pre-defined range. Every time a sensor is not able to report a value, or the combination of sensors values is out of this pre-defined range, the e-nose is not able to provide an answer. For these reasons, e-noses are small in number and mainly used in big organizations like hospitals or universities. Earlier prototypes of low price e-noses to be embedded in personal devices are showing less effectiveness in the sense that they are equipped with a lower number of sensors and each sensor has a narrower range of appliance.

There is a growing need for more advanced e-nose based diagnosis devices with more sophisticated methods, also for lower cost e-noses, which may have a limited measurement range.

SUMMARY

Provided herein, in one or more aspects, is a system for collaborating with electronic noses. The system includes a memory, and a processor communicatively coupled to the memory, wherein the system performs a method comprising: receiving a set of data from one e-nose of a plurality of e-noses, the set of data including a sensor identifier, a sensor output value, and a relevance flag for a predetermined diagnosis, wherein the relevance flag is indicative of a usefulness of the sensor output value for the predefined diagnosis; and determining a probability factor for the predetermined diagnosis based on the set of data, a relevance function, and a distribution function, wherein the relevance function is indicative of the relevance of the sensor output value for the predefined diagnosis, and the distribution function is indicative of a distribution of the sensor output value for the predefined diagnosis.

In a further aspect, a mobile diagnosis unit is provided which includes: a user interface to receive a predefined diagnosis; an e-nose sensor; a transmission unit to transmit a set of data, the set of data comprising a sensor identifier, a sensor output value, and a relevance flag for a predefined diagnosis, wherein the relevance flag is indicative of a usefulness of the sensor output value for the predefined diagnosis; a receiving unit to receive a total probability P(d) for the predefined diagnosis; and wherein the user interface provides notice of the total probability P(d) for the predefined diagnosis.

In a further aspect, a diagnosis method for collaborating using electronic noses is provided. The diagnosis method includes: receiving a set of data from one e-nose of a plurality of e-noses, the set of data comprising a sensor identifier, a sensor output value, and a relevance flag for a predefined diagnosis, wherein the relevance flag is indicative of a usefulness of the sensor output value for the predefined diagnosis; and determining a probability factor for the predefined diagnosis based on the set of data, a relevance function and a distribution function, wherein the relevance function is indicative of the relevance of the sensor output value for the predefined diagnosis, and the distribution function is indicative of a distribution of the sensor output value for the predefined diagnosis.

BRIEF DESCRIPTION OF THE DRAWINGS

Several embodiments of the invention are described below, by way of example only, with reference to the drawings, in which.

DETAILED DESCRIPTION

Figure 1:
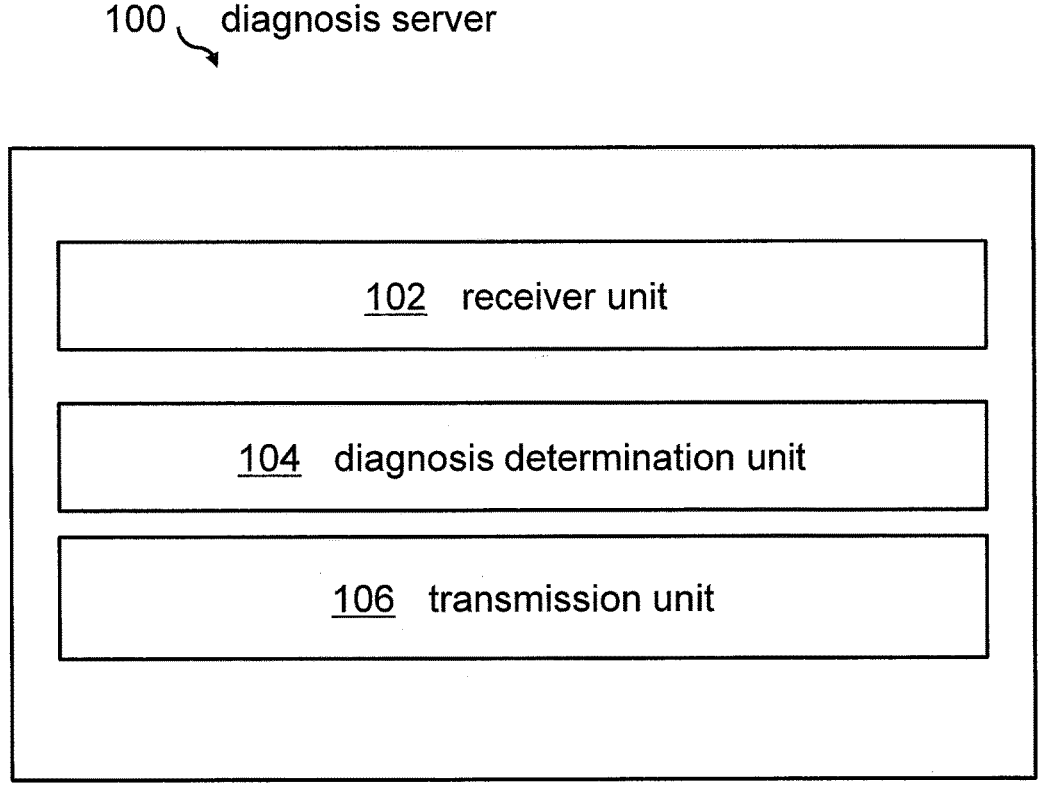
FIG. 1 shows an exemplary block diagram of a diagnosis server, in accordance with one or more aspects of the present invention.

In the context of this description, the following conventions, terms and/or expressions may be used:

The term "diagnosis server" may denote a component of a computer adapted to perform an analysis based on input from one or more sensor data. The sensor data may actually be measured sensor data. Additionally, earlier measured sensor data may have been stored in a database. The diagnosis server may comprise a number of sophisticated analysis algorithms functions. It may also incorporate none-sensor-data into the analysis determination.

The term "electronic nose" or, in short "e-nose" may denote a sensor, generating output signals, based on different chemical components present for the sensor. One e-nose may comprise several sensors. Different e-noses or different sensors in one e-nose may be required for different chemicals on different ranges of chemical concentrations. Another name for an e-nose may be "smell sensor". Different e-noses may be adapted to detect different chemical components in a gas mixture or an aerosol. An aerosol may be a suspension of fine solid particles or liquid droplets in a gas.

The term "diagnosis" may denote a certain or predefined state of health or illness of a person or an animal. A diagnosis may represent a determination regarding a certain health status.

The term "predefined diagnosis" may denote a guess for a diagnosis by a user of a mobile diagnosis unit. The user may input his guess for his actual diagnosis into the mobile diagnosis unit, whereby it becomes a predefined diagnosis. E.g., a predefined diagnosis may be "Cold?", meaning "do I have a cold", or does a person have a cold.

The term "relevance flag" may denote a flag being set to "0" or "1" by the mobile diagnosis unit. During a baseline measurement for the sensor(s), the usefulness of certain e-nose measurements including their respective output values may be set in relation to a certain diagnosis for a person. The mobile diagnosis unit may, e.g., comprise three sensors. It may turn out that the output values of the sensor 3 may not be useful for a diagnosis at all. However, sensor 2 of the three sensors may measure a chemical component that may be relevant and useful for the diagnosis, but the concentration of the chemical component to be measured may cause an out of range situation for the sensor. However, the usefulness of the sensor value may be set to "1", meaning "true". Indicators about the usefulness regarding a specific diagnosis may be handled within the mobile diagnosis unit. They may have been determined using server side computing of a diagnosis server. However, typically they are static in contrast to a dynamic probability determination based on a diagnosis server side diagnosis determination.

The proposed diagnosis server for collaborating with electronic noses, the mobile diagnosis unit for collaboration with a diagnosis server, the related devices in the related method may offer a couple of advantages:

Traditional mobile diagnosis units may rely on logic, incorporated into the mobile diagnosis unit. One or more e-noses may be used for a confirmation of a predefined diagnosis. However, such a method may not make effective usage of other diagnoses from other mobile diagnosis units and its respective users. The here disclosed devices and methods are based on a collaboration between a diagnosis server and a mobile diagnosis unit. The mobile diagnosis unit may have a plurality of e-noses and/or sensors, or there may be more than one mobile diagnosis units contributing to a final diagnosis. In addition, historic diagnoses may be reflected using sensor output values and respective diagnosis using a database as a basis for a relevance function and a distribution function.

A diagnosis being based on these two functions may be more precise than a single unit diagnosis system with fixed, static diagnosis patterns.

The interaction between a mobile diagnosis unit and a diagnosis server, in particular using cloud technologies, allows for an overall probability expression for a diagnosis for a person (or animal).

Such a technique may allow a community of people to build a relevance and distribution function for each disease, and associate the trouble the user may be experiencing, the time frame in which it happens, the geographical location, and other environmental parameters.

When a user may request an evaluation or diagnosis for a given measurement of a sensor of the e-nose, a diagnosis server side application may interpolate the provided measured data with an n-dimensional function of the disease in the community, to build a probabilistic report and correlate which diseases the values may be related to. The "experience of the cloud" may be used, so to speak.

If not enough information is available for a server side diagnosis, the user of the mobile diagnosis unit may be presented a list of questions for more information. Thus, the user and the system get in a dialogue helping to close information gaps for a most probable diagnosis. In case it is needed, the diagnosis server may inform the user about the most common troubles associated with the most probable disease in form of a checklist that the user may give a feedback on and further filter the results. For this purpose, the diagnosis system may transmit the related information from the diagnosis server to the mobile diagnosis unit.

The more users with mobile diagnosis units may be in collaboration with the diagnosis server, in particular wirelessly, and the more diagnoses may be performed, the more precise a probability for a predefined diagnosis may be performed. In this sense, a system comprising the diagnosis server and a plurality of mobile diagnosis units may be seen as a self-learning and optimizing system.

According to one embodiment of the diagnosis server, the set or sets of data may comprise in addition environmental data which comprise at least one out of the group consisting of a photo, a time stamp, geographical coordinates, temperature, humidity, altitude. This may add more decision criteria to algorithms available in the diagnosis server. Symptoms for a specific disease may vary according to temperature and/or high humidity and/or attitude. There may also be a concentration of specific diseases within a geographical region, so that a probability for a specific diagnosis for a person located in an environment of that geographical region may be higher. Using picture recognition and analysis, a diagnosis may be made more specific, e.g., for skin diseases.

According to a further embodiment of the diagnosis server each set of data receivable from the plurality of e-noses or sensors may be stored in a database for further reference, i.e., for future diagnoses. These future diagnoses may relate to predetermined diagnoses of the same person or other persons of the community. This way, the gained experience in the diagnosis server may be available for each community member. Additionally, a distribution function for all measured sensor output values in relationship to a specific diagnosis may be built. The same applies to a relevance function. A resulting probability factor for a diagnosis may be much more precise (see below).

According to an additional embodiment of the diagnosis server, the determination unit may be adapted to determine a value for the distribution function based on one or more of the sensor output values in comparison to all stored sensor output values in the database for the predefined diagnosis. The distribution function may basically represent a percentage of sensor values in the database having the same sensor output value for the same predefined diagnosis. This way, historically measured sensor output values in correlation with the predefined diagnosis may be correlated with an actual sensor output value of a given set of data. Again, the experience of the whole community may be used for a diagnosis determination.

According to a further enhanced embodiment of the diagnosis server, the determination unit may be adapted to determine the probability factor P(s) for a diagnosis based on $$P(s) = RF(v(s)) * DF(v(s)),$$

wherein
s=sensor identifier,
v(s)=sensor output value,
RF is the relevance function,
DF is the distribution function.

The relevance function and the distribution function, each being independent on the sensor output value of a specific sensor "s", may have values between "0" and "1". Thus, a resulting probability may also have a value between "0" and "1", expressing a correlation between a specific predetermined diagnosis and a specific sensor output value of their related sensor.

According to an even more advanced embodiment of the diagnosis server, the determination unit may be also adapted to determine the total probability P(d) for the predetermined diagnosis based on $$P(d)=P(s1)*P(s2)* \ldots *P(sm),$$

wherein
d=predetermined diagnosis,
s1=sensor 1, s2=sensor 2, sm=sensor m.

In this case, a plurality of sensor output values from a plurality of sensors may be involved. The source of the values may originate from different e-noses from one mobile diagnosis unit all from several different mobile diagnosis units. This may deliver a great flexibility in used e-noses and sensors. If, e.g., a user may have only a mobile diagnosis unit in, e.g., his mobile phone, and a user may also use a more advanced mobile diagnosis unit in a medical centre or a community centre, the additionally delivered sets of data to the diagnosis server for a predefined diagnosis may enhance the precision of the diagnosis.

The data for the different sensors within a given timeframe may be used for the relevance function, and thus, for the determination of the total probability P(d). It may also be noted that the relevance flag (from the mobile diagnosis unit) and the relevance function (from the diagnosis server) may be different entities with different functions.

According to one more embodiments of the diagnosis server, there may be a transmission unit available. It may be attached to the diagnosis server. The transmission unit may be adapted to transmit the total probability for a predetermined diagnosis, in particular, to the mobile unit in a wireless way. Moreover, the complete communication between a plurality of mobile diagnosis units and the diagnosis server may be based on any wireless or wire-based, or a mixture of both, communication.

According to one advantageous embodiment of the mobile diagnosis unit, it may comprise a plurality of e-nose sensors. Actually, each mobile diagnosis unit may have a different number of sensors. They may be optimized for detecting different chemical compounds.

According to one further embodiment of the mobile diagnosis unit, the set of data generated by the mobile diagnosis unit may comprise environmental data generated by at least one out of the group consisting of a camera, a clock, geographical coordinate sensor, temperature sensor, humidity sensor, altitude sensor. The effects have been discussed above already. In addition, it may be mentioned that the correlation between specific sensor output values and a predefined diagnosis may vary by the time of the day.

It should also be noted that embodiments of the invention have been described with reference to different subject-matters. In particular, some embodiments have been described with reference to method type claims whereas other embodiments have been described with reference to apparatus type claims. However, a person skilled in the art will gather from the above and the following description that, unless otherwise notified, in addition to any combination of features belonging to one type of subject-matter, also any combination between features relating to different subject-matters, in particular, between features of the method type claims, and features of the apparatus type claims, is considered as to be disclosed within this document.

The aspects defined above and further aspects of the present invention are apparent from the examples of embodiments to be described hereinafter and are explained with reference to the examples of embodiments, but to which the invention is not limited.

In the following, a detailed description of the figures will be given. All instructions in the figures are schematic. Firstly, a block diagram of an embodiment of the inventive diagnosis server for collaborating with electronic noses, and mobile diagnosis units for collaboration with a diagnosis server is given. Afterwards, further embodiments and a diagnosis method for collaborating with electronic noses are described.

FIG. 1 shows an exemplary block diagram of a diagnosis server 100. The diagnosis server 100 may comprise a receiver unit 102 adapted to receive a set of data receivable from one out of a plurality of e-noses. Some of the e-nose measurement values may originate from one mobile diagnosis unit, and others may originate from several mobile diagnosis units.

The received set of data may comprise a sensor identifier, in particular a unique identifier of a specific sensor. All sensors may have their unique identifier. The set of data may also comprise a sensor output value, in particular a measured value indicative of a measured concentration of a chemical compound. Furthermore, the set of data may also comprise a relevance flag for a predefined diagnosis. A user may have to put in the predetermined diagnosis as a question. The input may have been done in several ways: by typing on a keyboard, by typing on a touch-sensitive user interface, by voice recognition, by gesture recognition, by selecting from a menu within a user interface, and the like.

The relevance flag may be a general indication for the usefulness of a specific sensor output for a predefined diagnosis. Such a relevance indication may be stored in the mobile diagnosis unit. It may be sensor and/or diagnosis dependent. Values of the relevance flag may be "0"—meaning not relevant for a predefined diagnosis—or "1" meaning relevant for a predefined diagnosis.

Thus, the relevance flag may be indicative of a usefulness of the sensor output value for the predefined diagnosis. However, the sensor may be out of range for a useful measurement meaning that the sensor output value may be useless in such a case, but the relevance flag may still be "true".

Moreover, the diagnosis server may comprise a (diagnosis) determination unit 104 adapted for determining a probability factor for the predefined diagnosis based on the set of data, a relevance function and a distribution function, as explained above. The relevance function may be indicative of the relevance of the sensor output value for the predefined diagnosis. The distribution function may be indicative of a distribution of the sensor output value for the predefined diagnosis.

Furthermore, a transmission unit may be available as discussed below in context of FIG. 3.

Figure 2:
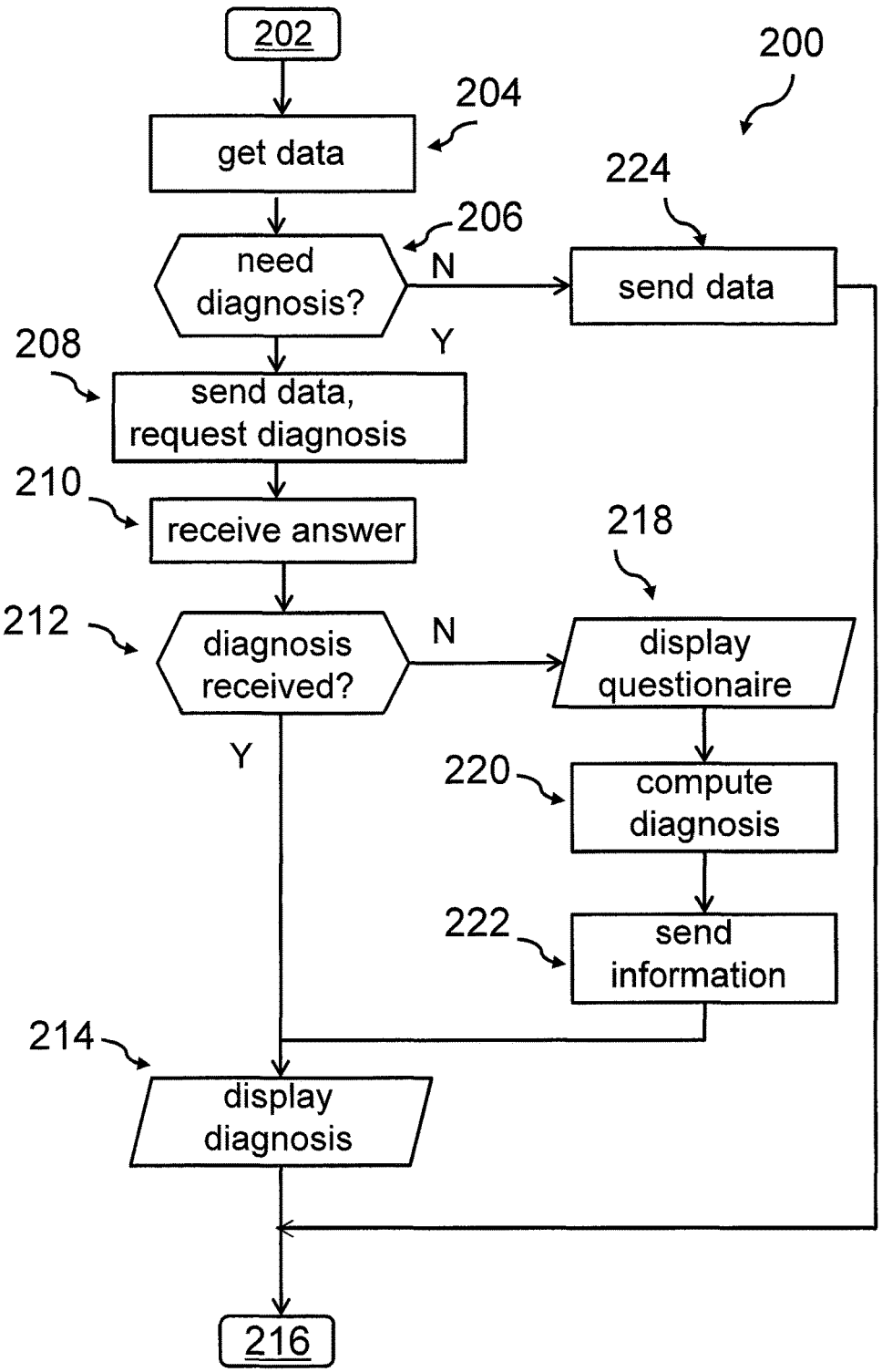
FIG. 2 shows an exemplary block diagram a process flow on a mobile diagnosis unit, in accordance with one or more aspects of the present invention.

FIG. 2 shows an exemplary block diagram and process flow 200 on the mobile diagnosis unit side. A related software program may start at 202. Firstly, the unit may have to obtain data, 204: a) sensor data and b) a diagnosis question. A user may select a diagnosis question relating to a specific diagnosis. This may be performed by free text input or by selecting from a menu in the user interface. Moreover, voice input may be possible. The received spoken word for the diagnosis question may be analyzed and recognized either on the mobile unit or on a related server system. Next, at 206, it may be decided whether a specific diagnosis is required. If not, the received values from the e-nose sensor may be sent, 224, or transmitted to a related diagnosis server 100 (FIG. 1). Here, the data may be stored for further reference and/or for baseline measurement. The program may end at 216.

In case a user requests a specific diagnosis, the sensor data may be sent, 208, to the diagnosis server 100 (FIG. 1). Together with a sensor data, sensor identifier and a relevance flag for the specified diagnosis may also be sent to the diagnosis server.

At the diagnosis server 100 (FIG. 1) side, an answer may be determined and may be received by the mobile diagnosis unit, 210. If a diagnosis has been received because the server has determined that the diagnosis is unique, then the result of the diagnosis may be displayed, 214, at the mobile diagnosis unit. The program may end at 216.

In case the received answer from the diagnosis server 100 (FIG. 1) may not be a unique diagnosis, the diagnosis server 100 may send a series of questions such that a questionnaire may be displayed at 218 to the user.

A couple more steps (not shown in the flowchart) may be required: the user may answer the questions, the questions may be transmitted to the diagnosis server 100 (FIG. 1), the diagnosis server 100 may be re-determining its diagnosis and may send it back to the mobile diagnosis unit. In case the re-determined diagnosis is received from the server, (same as 212), the diagnosis may be displayed, 214.

Alternatively, the mobile diagnosis unit may compute the diagnosis itself, 220, and send information back, 222, to the diagnosis server 100 (FIG. 1). It may also be possible that the mobile diagnosis unit may receive instructions, e.g., in form of a markup language, how to compute, 220, the diagnosis.

Figure 3:
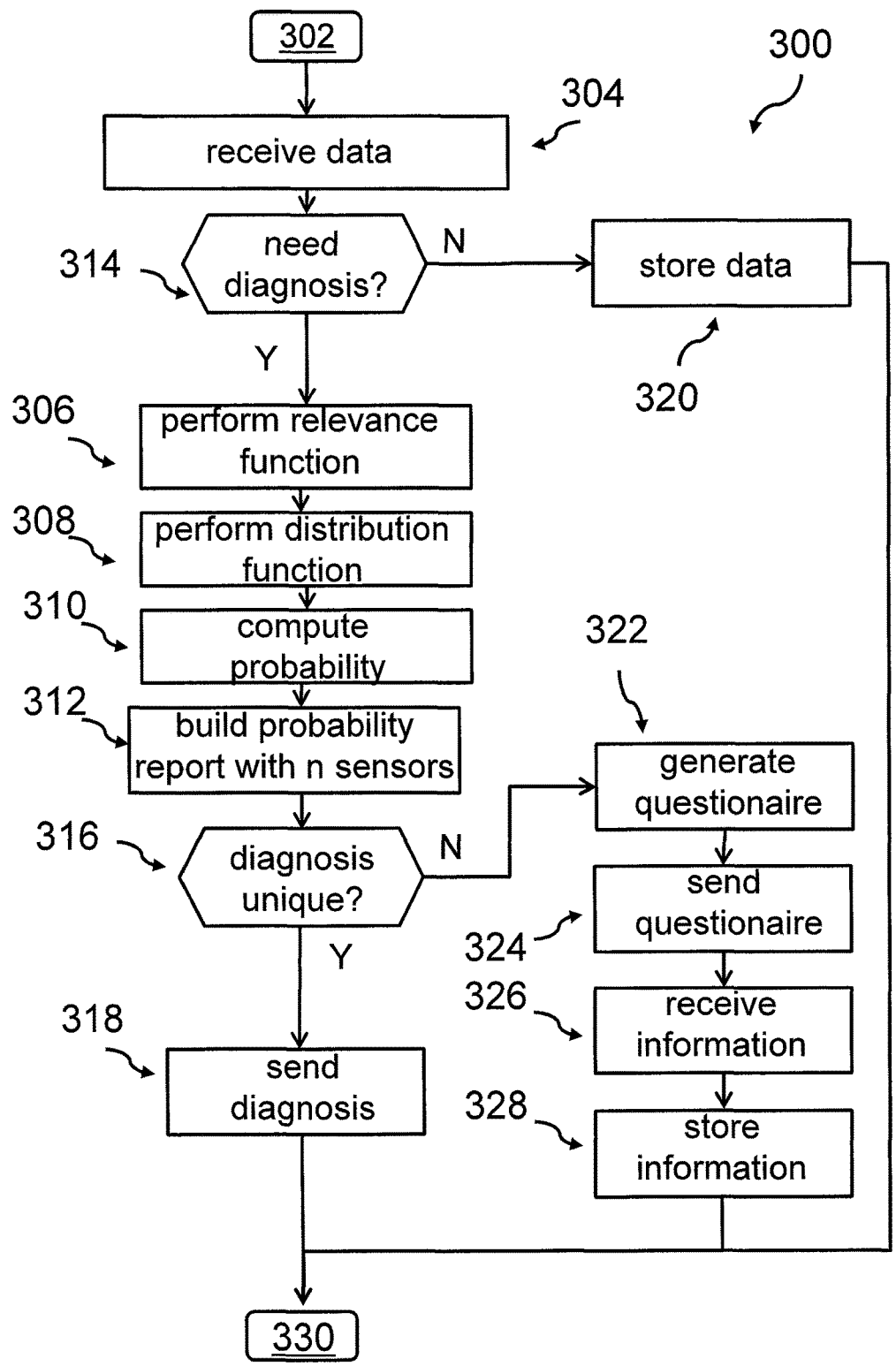
FIG. 3 shows an exemplary block diagram and process flow on a diagnosis server, in accordance with one or more aspects of the present invention.

FIG. 3 shows an exemplary flowchart 300 executed by a control system as part of the diagnosis server 100 (FIG. 1). The program starts at 302. Firstly, the system may receive data, 304, from the mobile diagnosis unit. The data may comprise data only or, there may also be a diagnosis request included. As a minimum, the server may receive a sensor output value from sensor m, together with an identifier of sensor m, as well as optionally a related relevance flag for a predefined diagnostic. This may be received by the diagnosis server 100 (FIG. 1) in a data set. In case no diagnosis may be requested, the data may be stored for later reference, 320, in a database of the diagnosis server. This may comprise not only the sensor value, but also other received information like a sensor identifier, and other environmental data like geographical position (GPS coordinates), geographical altitude, humidity, temperature, a timestamp and/or a photo. After that, the program may end at 330.

In case a diagnosis may be requested, the next steps may be performed: the relevance function, 306, and the distribution function, 308, may be calculated. Additionally, in step 310, the probability P(d) for a predetermined diagnosis may be calculated, 312. For this, the values of additional sensors may be used, as explained above. All results may be built into a probability report for the diagnosis based on n sensor values and also values from the database of earlier sensor values and related diagnoses.

If a diagnosis has been requested, 314, by the mobile diagnosis unit and the computed diagnosis of the diagnosis server 100 (FIG. 1) may be unique, 316, then the diagnosis server may send the results of the diagnosis computation to the mobile diagnosis unit, 318. This may be done using the transmission unit 106 (see FIG. 1). The program may end at 330.

In case the diagnosis may not be unique, 316, the diagnosis server may generate, 322, a questionnaire to be sent, 324, to the mobile diagnosis unit via the transmission unit 106 of the diagnosis server 100 (see FIG. 1). All transmissions from the mobile diagnosis unit to the diagnosis server and back may be performed wirelessly using a public or private wireless network. At the mobile diagnosis unit, the questions of the questionnaire may be answered and sent back to the diagnosis server, were they may be received, 326.

A couple more steps (not shown in the flowchart) may be required: the diagnosis server 100 may be re-determining its diagnosis and may send it back to the mobile diagnosis unit. The re-determined diagnosis may be then received (212) and displayed on the mobile display unit (214).

Also this information may be stored, 328, in the database of the diagnosis server 100 (FIG. 1). It may be used to further reference for another diagnosis. The program may end at 330.

FIG. 1 shows an exemplary block diagram of an embodiment of mobile diagnosis unit 400. The mobile diagnosis unit 400 for collaboration with a diagnosis server 100 (FIG. 1) may comprise a user interface 402 adapted for receiving a predetermined diagnosis and other input. A user may choose a variety of ways to input the predefined diagnosis. A non-complete list of examples may comprise: using a keyboard or a touch-sensitive screen, using voice input or selecting from a menu. Also, more sophisticated gesture input and/or gesture recognition is possible.

Moreover, the mobile diagnosis unit 400 may also comprise at least e-nose sensor 404 and a transmission unit 406 adapted to transmit a set of data and related data. The set of data may comprise a sensor 404 identifier, a sensor 404 output value, and a relevance flag for a predefined diagnosis, as defined above.

A receiving unit 408 may be adapted to receive a total probability P(d) for the predetermined diagnosis, in particular from the diagnosis server 100 (FIG. 1). The communication between the unit and the server may be performed wirelessly or, wire based.

The user interface 402 may also be adapted to notify about the total probability P(d) for the predefined diagnosis. In particular, the "notify about" may be made to a user. A display may be instrumental for such a purpose. However, also voice output or, tactile output using special devices for disabled people may be possible, just to name a few.

It may be noted here, that the relevance flag is something not statically derived by the sensor 404 output value. It's like a second level analysis about how much that sensor 404 is relevant for the given diagnosis. It may also happen, for example, that the sensor 404 output value is not in the range for a diagnosis, but its relevance flag may be true.

The following scenario may be helpful in this context: Every time a measurement may show a value for a sensor 404 that may be out of range for a given diagnosis, the diagnosis itself may not be evaluated positively (for example, if the e-nose is queried for a certain disease and s2 may show a value that may not be in the range for that disease, the e-nose may answer that the user may not be affected by it). However, among all the measurements leading to negative diagnosis, there may be cases in which some of the sensors 404 of an e-nose show values in a range for a given disease. For example, if someone wants to check his breath for a disease D1 and he uses a traditional e-nose, or if he uses a personal device and he knows he is not affected, he may have s2 and s4 in range for D1, and all other sensors 404 out of range. So, the answer will be negative (he is not affected by D1) but the system may compute s2 and s4 as "not relevant" for D1, while the other sensors 404 may be relevant. The relevance of a sensor 404 may be computed also in another case. During the personal device life, a series of measurements may be performed by a user in a good health state, and a range of "normal" values for each sensor 404 is built for him and stored in a database. As soon as an "out of range" value is detected, a warning is issued and (likely) the user will perform some exams or will directly enter the disease he's suffering, together with the troubles he's experiencing. In this case, the system will consider the out of range sensor(s) 404 as relevant for that disease, even for diseases for which the e-nose is not meant to provide any answer.

Figure 4:
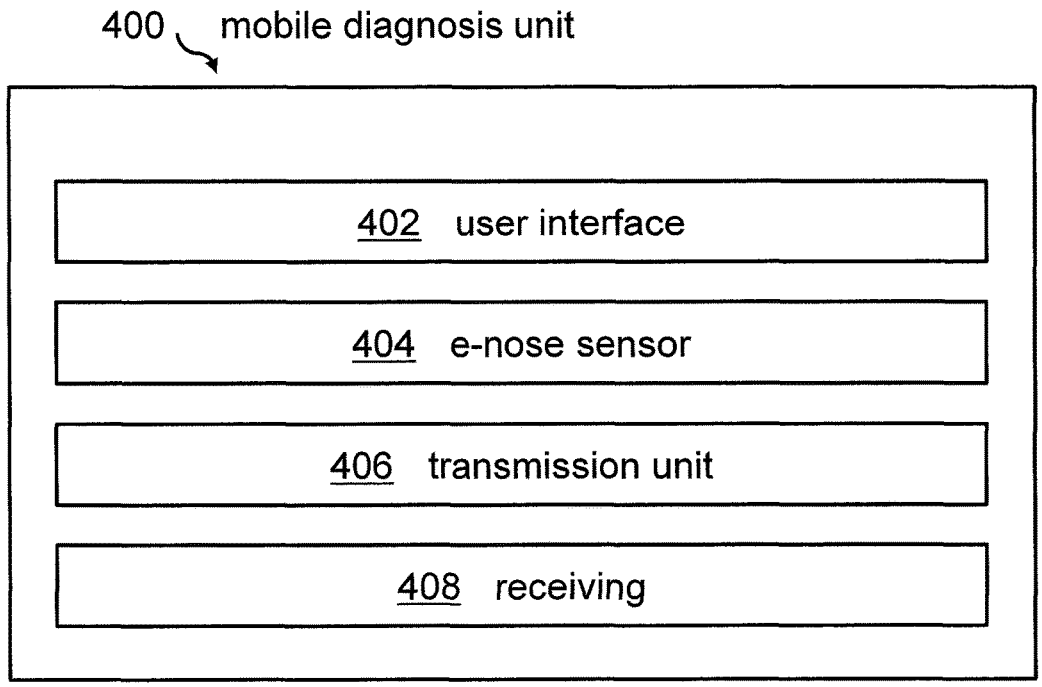
FIG. 4 shows an exemplary block diagram of an embodiment of a mobile diagnosis unit, in accordance with one or more aspects of the present invention.
Figure 5:
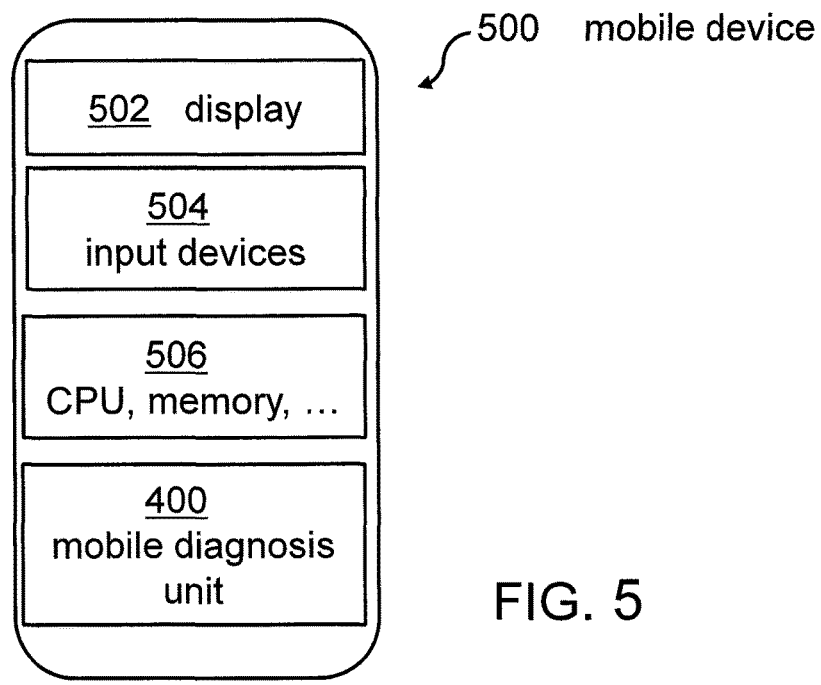
FIG. 5 shows an exemplary block diagram of an embodiment of a mobile phone comprising a mobile diagnosis unit, in accordance with one or more aspects of the present invention.

FIG. 5 shows a mobile device 500, like a smart phone, equipped with a mobile diagnosis unit 400 (FIG. 4). The mobile device 500 may comprise a touch sensitive display unit 502. In this case, the screen of the display unit 502 may also be used for user input. Additionally, the mobile device 500 may comprise keys or other switches 504 for input purposes. Furthermore, the mobile device 500 may be equipped with a central possessing unit, memory, a battery, and other elements typically are for today's mobile devices, like smart phones. All of these additional elements may be referred to by reference number 506. Additionally, the mobile device 500 may comprise the mobile diagnosis unit 400 (FIG. 4). The mobile device 500 and the mobile diagnosis unit 400 (FIG. 4) may use common element. For example, the receiving unit 408 (FIG. 4) of the mobile diagnosis unit 400 and/or the transmission unit 406 may be equivalent to those elements of the mobile device 500 (FIG. 5). However, the transmission unit 406 and a receiving unit 408 may also be seen as an integral part of the mobile diagnosis unit. In this case, there may be an interface between the mobile device 500 and the mobile diagnosis unit being adapted for handling the transmission and receiving.

Figure 6:
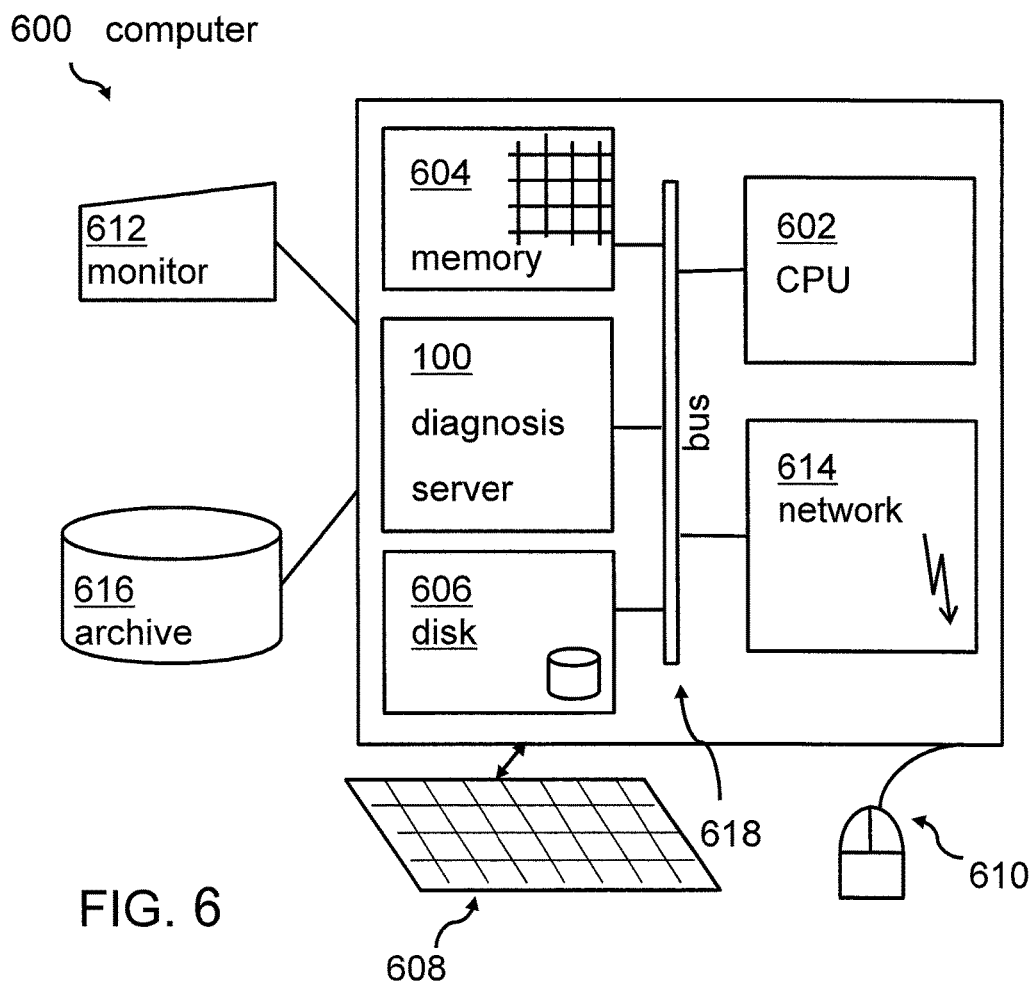
FIG. 6 shows a block diagram of an embodiment of a computer comprising a diagnosis server, in accordance with one or more aspects of the present invention.

FIG. 6 shows a block diagram of a computing system 600 with typical elements also comprising the diagnosis server 100 (FIG. 1).

Embodiments of the invention may be implemented together with virtually any type of computer, regardless of the platform being suitable for storing and/or executing program code. For example, as shown in FIG. 6, a computing system 600 may include one or more processor(s) 602 with one or more cores per processor, associated memory elements 604, an internal storage device 606 (e.g., a hard disk, an optical drive such as a compact disk drive or digital video disk (DVD) drive, a flash memory stick, a solid-state disk, etc.), and numerous other elements and functionalities, typical of today's computers (not shown). The memory elements 604 may include a main memory, e.g., a random access memory (RAM), employed during actual execution of the program code, and a cache memory, which may provide temporary storage of at least some program code and/or data in order to reduce the number of times, code and/or data must be retrieved from a long-term storage medium or external bulk storage (archive 616) for an execution. Elements inside the computer 600 may be linked together by means of a bus system 618 with corresponding adapters. As shown, the diagnosis server may also be attached to the bus system 618. However, it may also be integrated into the computer 600 in a different, e.g., distributed form.

The computing system 600 may also include input means, such as a keyboard 608, a pointing device such as a mouse 610, or a microphone (not shown). Alternatively, the computing system may be equipped with a touch sensitive screen as main input device. Furthermore, the computer 600, may include output means, such as a monitor or screen 612, (for instance, a liquid crystal display (LCD), a plasma display, a light emitting diode display (LED), or cathode ray tube (CRT) monitor). The computer system 600 may be connected to a network (e.g., a local area network (LAN), a wide area network (WAN), such as the Internet or any other similar type of network, including wireless networks via a network interface connection 614. This may allow a coupling to other computer systems or a storage network or a tape drive. Those, skilled in the art will appreciate that many different types of computer systems exist, and the aforementioned input and output means may take other forms. In general, the computer system 600 may include at least the minimal processing, input and/or output means, necessary to practice one or more embodiments of the present invention.

Actually, the mobile phone 500 (FIG. 5) may be equipped with basically the same active elements as the diagnosis server 100 (FIG. 1). Only the size of the active computing elements may be adapted to the size of the mobile phone. Instead of the diagnosis server 100 (FIG. 1), the mobile phone may be equipped with the mobile diagnosis unit 400 (FIG. 4). And instead of a pointing device 610, a touch sensitive screen may take over an equivalent function. The keyboard 608 may also be replaced by a touch sensitive screen as a personal with ordinary skills may know.

Figure 7:
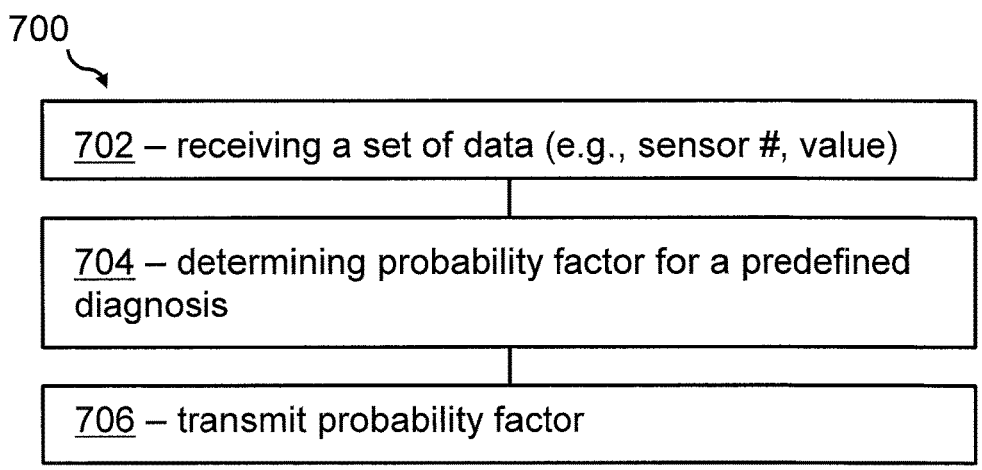
FIG. 7 shows a block diagram of a method for collaborating with electronic noses, in accordance with one or more aspects of the present invention.

FIG. 7 shows a block diagram of a diagnosis method 700 for collaborating using electronic noses. The diagnosis method 700 may comprise receiving, 702—e.g., at a diagnosis server 100—a set of data receivable from one out of a plurality of e-noses 404 (FIG. 4). The set of data may comprise a sensor 404 identifier, a sensor 404 output value, and a relevance flag for a predefined diagnosis. Also here, the relevance flag may indicative of a usefulness of the sensor 404 output value for the predefined diagnosis.

Moreover, the method may comprise determining, 704, a probability factor for the predefined diagnosis based on the set of data, a relevance function and a distribution function. The relevance function may be indicative of the relevance of the sensor 404 output value for the predefined diagnosis, and the distribution function may be indicative of a distribution of the sensor 404 output value for the predefined diagnosis.

After the determination 704, the probability factor for a predetermined diagnosis may be transmitted, 706, in particular to a mobile unit and/or a diagnosis unit.

As described above, a diagnosis server is provided herein for collaboration with electronic noses, a mobile diagnosis unit, and a diagnosis method for collaborating with electronic noses according to the claims. Parts of the solution may also be embedded into a computer, a mobile phone or a system.

According to one embodiment, a diagnosis server for collaboration with electronic noses may be provided. The diagnosis server may comprise a receiver unit adapted to receive a set of data receivable from one out of a plurality of e-noses. Each set of data may comprise a sensor identifier, a sensor output value, and a relevance flag for a predefined diagnosis. The relevance flag may be indicative of a usefulness of the sensor output value for the predefined diagnosis.

The diagnosis server may also comprise a determination unit adapted for determining a probability factor for the predefined diagnosis based on the set of data, a relevance function and a distribution function. The relevance function may be indicative of the relevance of the sensor output value for the predefined diagnosis, and the distribution function may be indicative of a distribution of the sensor output values for the predefined diagnosis.

According to another embodiment, a mobile diagnosis unit for collaboration may be provided. The mobile diagnosis unit may comprise a user interface adapted to receive a predetermined diagnosis, an e-nose sensor, and a transmission unit adapted to transmit sets of data. Each set of data may comprise a sensor identifier, a sensor output value, and a relevance flag for a predefined diagnosis. The relevance flag may be indicative of a usefulness of the sensor output value for the predefined diagnosis.

The mobile diagnosis unit may also comprise a receiving unit adapted to receive a total probability P(d) for the predetermined diagnosis, in particular from a diagnosis server. The user interface may also be adapted to notify about the total probability P(d) for the predefined diagnosis, in particular to a user of the mobile diagnosis unit.

It may be noted that the mobile diagnosis unit may comprise more than one sensor and from each sensor a set of data may be provided.

According to yet another embodiment, a diagnosis method for collaborating with electronic noses may be provided. The diagnosis method may comprise receiving a set of data receivable from one out of a plurality of e-noses. The sets of data may each comprise a sensor identifier, a sensor output value, and a relevance flag for a predefined diagnosis. The relevance flag may be indicative of a usefulness of the sensor output value for the predefined diagnosis.

The method may additionally comprise determining a probability factor for the predefined diagnosis based on the set, or in particular sets of data, a relevance function and a distribution function. The relevance function may be indicative of the relevance of the sensor output value for the predefined diagnosis. The distribution function is indicative of a distribution of the sensor output value for the predefined diagnosis.

Furthermore, a diagnosis system, comprising the diagnosis server and the mobile diagnosis unit, as well as a mobile phone comprising the mobile diagnosis unit, and a computer comprising the diagnosis server, may be provided.

It may be noted that the function of the diagnosis server may be delivered as a cloud computing service, wherein the diagnosis server may serve a plurality of mobile diagnosis units using standardized Web protocols. The capability provided to a consumer, e.g., a user of a mobile diagnosis unit may be to use the provider's applications running on a cloud infrastructure. The applications may be accessible from various client devices, in particular, mobile diagnosis units, through a thin client interface such as a Web browser. The consumer may not manage or control the underlying cloud infrastructure including network, servers, operating systems, storage, or even individual application capabilities, with the possible exception of limited user-specific application configuration settings. The provider's service may be based on the disclosed diagnosis server.

While the invention has been described with respect to a limited number of embodiments, those skilled in the art, having benefit of this disclosure, will appreciate that other embodiments may be devised, which do not depart from the scope of the invention, as disclosed herein. Accordingly, the scope of the invention should be limited only by the attached claims. Also, elements described in association with different embodiments may be combined. It should also be noted that reference signs in the claims should not be construed as limiting elements.

As will be appreciated by one skilled in the art, aspects of the present disclosure may be embodied as a system, method or computer program product. Accordingly, aspects of the present disclosure may take the form of an entirely hardware embodiment, an entirely software embodiment (including firmware, resident software, micro-code, etc.) or an embodiment combining software and hardware aspects that may all generally be referred to herein as a "circuit," "module" or "system." Furthermore, aspects of the present disclosure may take the form of a computer program product embodied in one or more computer readable medium(s) having computer readable program code embodied thereon.

Any combination of one or more computer readable medium(s) may be utilized. The computer readable medium may be a computer readable signal medium or a computer readable storage medium. A computer readable storage medium may be, for example, but not limited to, an electronic, magnetic, optical, electromagnetic, infrared, or semiconductor system, apparatus, or device, or any suitable combination of the foregoing. More specific examples (a non-exhaustive list) of the computer readable storage medium would include the following: an electrical connection having one or more wires, a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device, a magnetic storage device, or any suitable combination of the foregoing. In the context of this document, a computer readable storage medium may be any tangible medium that may contain, or store a program for use by or in connection with an instruction execution system, apparatus, or device.

A computer readable signal medium may include a propagated data signal with computer readable program code embodied therein, for example, in baseband or as part of a carrier wave. Such a propagated signal may take any of a variety of forms, including, but not limited to, electromagnetic, optical, or any suitable combination thereof. A computer readable signal medium may be any computer readable medium that is not a computer readable storage medium and that may communicate, propagate, or transport a program for use by or in connection with an instruction execution system, apparatus, or device.

Program code embodied on a computer readable medium may be transmitted using any appropriate medium, including but not limited to wireless, wireline, optical fiber cable, RF, etc., or any suitable combination of the foregoing.

Computer program code for carrying out operations for aspects of the present invention may be written in any combination of one or more programming languages, including an object oriented programming language such as Java, Smalltalk, C++ or the like and conventional procedural programming languages, such as the "C" programming language or similar programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider).

Aspects of the present disclosure are described with reference to flowchart illustrations and/or block diagrams of methods, apparatus (systems) and computer program products according to embodiments of the present disclosure. It will be understood that each block of the flowchart illustrations and/or block diagrams, and combinations of blocks in the flowchart illustrations and/or block diagrams, may be implemented by computer program instructions. These computer program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks.

These computer program instructions may also be stored in a computer readable medium that may direct a computer, other programmable data processing apparatus, or other devices to function in a particular manner, such that the instructions stored in the computer readable medium produce an article of manufacture including instructions, which implement the function/act specified in the flowchart and/or block diagram block or blocks.

The computer program instructions may also be loaded onto a computer, other programmable data processing apparatus, or other devices to cause a series of operational steps to be performed on the computer, other programmable apparatus or other devices to produce a computer implemented process such that the instructions, which execute on the computer or other programmable apparatus provide processes for implementing the functions/acts specified in the flowchart and/or block diagram block or blocks.

The block diagrams in the Figures illustrate the architecture, functionality, and operation of possible implementations of systems, methods and computer program products according to various embodiments of the present disclosure. In this regard, each block in the block diagrams may represent a module, segment, or portion of code, which comprises one or more executable instructions for implementing the specified logical function(s). It should also be noted that, in some alternative implementations, the functions discussed hereinabove may occur out of the disclosed order. For example, two functions taught in succession may, in fact, be executed substantially concurrently, or the functions may sometimes be executed in the reverse order, depending upon the functionality involved. It will also be noted that each block of the block diagrams, and combinations of blocks in the block diagrams, may be implemented by special purpose hardware-based systems that perform the specified functions or acts, or combinations of special purpose hardware and computer instructions.

The terminology used herein is for the purpose of describing particular embodiments only and is not intended to limit of the invention. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

The corresponding structures, materials, acts, and equivalents of all means or steps plus function elements in the claims below are intended to include any structure, material, or act for performing the function in combination with other claimed elements, as specifically claimed. The description of the present invention has been presented for purposes of illustration and description, but is not intended to be exhaustive or limited to the invention in the form disclosed. Many modifications and variations will be apparent to those of ordinary skills in the art without departing from the scope and spirit of the invention. The embodiment was chosen and described in order to best explain the principles of the invention and the practical application, and to enable others of ordinary skills in the art to understand the invention for various embodiments with various modifications, as are suited to the particular use contemplated.

The invention claimed is:

1. A system for collaborating with electronic noses, the system comprising:
   a memory; and
   a processor communicatively coupled to the memory, wherein the system performs a method comprising:
      receiving, by the processor, during a given time interval, a set of data from one e-nose of a plurality of e-noses, the set of data including:
         one or more sensor identifiers of one or more sensors;
         one or more sensor output values, each sensor output value originating from a sensor of the one or more sensors; and
         a relevance flag for a predefined diagnosis, wherein the relevance flag is indicative of a usefulness of the sensor output value for the predefined diagnosis for each of the one or more sensors, wherein for each sensor, the relevance flag for the predefined diagnosis is a static value, set, by the processor, upon performing a baseline measurement of the sensor, wherein the baseline measurement comprises an evaluation of respective output values on the sensor, in relation to the predefined diagnosis, and wherein the relevance flag for the predefined diagnosis for each of the one or more sensors comprises either a first value or a second value, the first value indicating that the sensor output of a sensor of the one or more sensors is not relevant for the predefined diagnosis, and the second value indicating that the sensor output of the sensor of the one or more sensors is relevant for the predefined diagnosis;
      storing, by the processor, the sensor output values and additional sensor output values received from additional e-noses of the one plurality of e-noses correlated with the predefined diagnosis;
      determining a relevance function, wherein the relevance function is indicative of the relevance of a sensor output value for a given sensor of the one or more sensors for the predefined diagnosis, wherein a basis of the relevance function is a database comprising historic diagnoses reflected using sensor output values, and wherein the relevance function and the relevance flag are different entities with different functions, and wherein the relevance function is derived from data originating from more than one sensor over a given timeframe;

determining a distribution function, wherein the distribution function is indicative of a distribution of the sensor output value for the given sensor of the one or more sensors for the predefined diagnosis, wherein the distribution function comprises a pre-defined portion of stored sensor output values having an equivalent sensor output value to the sensor output value for the given sensor of the one or more sensors, during the given time interval, for the predefined diagnosis;

determining a probability factor for the predefined diagnosis based on the set of data, the relevance function and the distribution function, generating a probability report for the predetermined diagnosis, utilizing the sensor output values and additional sensor output values received from the additional e-noses of the one plurality of e-noses correlated with the predefined diagnosis, and the probability factor; and transmitting the probability report and the probability factor for the predetermined predefined diagnosis to a user interface adapted to notify a user of the probability factor, wherein the probability factor includes an indication of usefulness, based on the relevance flags of the one or more sensors utilized to determine the probability factor.

2. The system of claim 1, wherein the set of data comprises environmental data selected from the group consisting of: at least one of a photo, a time stamp, geographical coordinates, temperature, humidity, and altitude.

3. The system of claim 1, wherein the determining ascertains the probability factor P(s) for the given sensor of the one or more sensors based on:

$$P(s)=RF(v(s))*DF(v(s)),$$

wherein
s=sensor identifier;
v(s)=sensor output value;
RF is the relevance function; and
DF is the distribution function, wherein the relevance function and the distribution function each consist of a value between 0 and 1, wherein the relevance function indicates a relevance of the sensor output value for the predefined diagnosis, wherein the relevance value is derived from data originating from more than one sensor over a given timeframe, and wherein the probability factor expressing a correlation between the predetermined diagnosis and the sensor output value of a sensor from which the sensor output value is output.

4. The system of claim 3, further comprising:
determining a total probability P(d) for a predetermined diagnosis based on multiplying probability factors of each sensor of the one or more sensors together.

5. The system of claim 4, further comprising transmitting the total probability for the predetermined diagnosis.

6. The system of claim 5, wherein at least one of the receiving the set of data or the transmitting the total probability comprises wirelessly receiving or wirelessly transmitting, respectively.

* * * * *